(12) United States Patent
Evans et al.

(10) Patent No.: US 9,345,423 B2
(45) Date of Patent: May 24, 2016

(54) METHOD FOR MEASURING BREATH ALCOHOL CONCENTRATION AND APPARATUS THEREFOR

(71) Applicant: ALCO SYSTEMS SWEDEN AB, Järfälla (SE)

(72) Inventors: Nigel Evans, South Glamorgan (GB); Leigh Wallington, South Glamorgan (GB)

(73) Assignee: Alco Systems Sweden AB, Järfälla (SE)

( * ) Notice: Subject to any disclaimer, the term of this patent is extended or adjusted under 35 U.S.C. 154(b) by 0 days.

(21) Appl. No.: 14/409,062

(22) PCT Filed: Jun. 18, 2013

(86) PCT No.: PCT/SE2013/050722
§ 371 (c)(1),
(2) Date: Dec. 18, 2014

(87) PCT Pub. No.: WO2013/191634
PCT Pub. Date: Dec. 27, 2013

(65) Prior Publication Data
US 2015/0335265 A1 Nov. 26, 2015

(30) Foreign Application Priority Data

Jun. 19, 2012 (SE) ...................................... 1250659

(51) Int. Cl.
*G01N 33/497* (2006.01)
*A61B 5/097* (2006.01)
(Continued)

(52) U.S. Cl.
CPC .................. *A61B 5/082* (2013.01); *A61B 5/087* (2013.01); *A61B 5/097* (2013.01); *A61B 5/742* (2013.01);
(Continued)

(58) Field of Classification Search
CPC .............. G01N 33/4972; G01N 33/98; G01N 33/0006; G01N 33/497; A61B 5/097; A61B 5/087; A61B 5/742; A61B 5/7225; A61B 5/083

USPC ......... 436/900; 422/84, 83, 50; 600/532, 529, 600/300
See application file for complete search history.

(56) References Cited

U.S. PATENT DOCUMENTS 4,487,055 A * 12/1984 Wolf .................. G01N 33/4972
422/84
4,770,026 A 9/1988 Wolf
(Continued)

FOREIGN PATENT DOCUMENTS

CA 2552130 A1 1/2007
GB 2201245 A 8/1988
(Continued)

OTHER PUBLICATIONS

European Patent Office (ISA/EP), International Search Report from PCT/SE2013/050722 as completed Aug. 12, 2013.
(Continued)

*Primary Examiner* — Christine T Mui
(74) *Attorney, Agent, or Firm* — Barclay Damon, LLP

(57) ABSTRACT

A method and apparatus for measuring user breath alcohol concentration. A flow of an expired breath sample is passed through a fuel cell sensor giving an output signal proportional to the amount of alcohol present in the sample. By measuring pressure, the volume of the sample may be calculated by integrating pressure over expiration time of the sample, whereas breath alcohol concentration is calculated based on the fuel cell output signal. Both sample volume and breath alcohol concentration values are continually updated by integrating measured instantaneous pressure and fuel cell output signal over time, irrespective of breath sample volume. When the user stops blowing, volume compensation is performed to obtain a compensated fuel cell output signal using a stored calibration volume. Hence, an improved method for accurately measuring breath alcohol concentration of a user is achieved, capable of handling varied expired volumes of breath, obviating the need for sampling mechanism.

17 Claims, 2 Drawing Sheets

(51) Int. Cl.
    A61B 5/085    (2006.01)
    G01N 33/98    (2006.01)
    G01N 33/48    (2006.01)
    A61B 5/08     (2006.01)
    A61B 5/087    (2006.01)
    A61B 5/00     (2006.01)
    B60W 40/08    (2012.01)

(52) U.S. Cl.
    CPC .......... B60W 40/08 (2013.01); G01N 33/4972 (2013.01); *A61B 2560/0223* (2013.01); *B60W 2040/0836* (2013.01); *G01N 33/48* (2013.01); *G01N 33/497* (2013.01); *G01N 33/98* (2013.01)

(56) References Cited

U.S. PATENT DOCUMENTS

| 5,612,896 | A  |   | 3/1997 | Stock |
|---|---|---|---|---|
| 6,167,746 | B1 |   | 1/2001 | Gammenthaler |
| 7,422,723 | B1 | * | 9/2008 | Betsill ................ G01N 33/4972 422/411 |
| 2003/0176803 | A1 |   | 9/2003 | Gollar |
| 2003/0183437 | A1 |   | 10/2003 | Mendoza |
| 2005/0241871 | A1 |   | 11/2005 | Stewart et al. |
| 2005/0251060 | A1 | * | 11/2005 | Gollar .................. A61B 5/097 600/532 |
| 2011/0009765 | A1 |   | 1/2011 | Gollar |

FOREIGN PATENT DOCUMENTS

| JP | 2004522944 A | 7/2004 |
|---|---|---|
| JP | 2014-507632 A | 3/2014 |
| WO | WO2012087187 A1 | 6/2012 |

OTHER PUBLICATIONS

European Patent Office (ISA/EP), International Preliminnary Report on Patentability with Notification of Transmittal of same dated May 30, 2014 (total 14 pgs.).

Japanese Patent Office, Office Action in JP Patent Application No. 2015-518377 dated Aug. 4, 2015 (English Translation, 3 pages).

Chinese Patent Office, Office Action in CN Patent Application No. 201300327657, dated Jul. 2015.

* cited by examiner

METHOD FOR MEASURING BREATH ALCOHOL CONCENTRATION AND APPARATUS THEREFOR

CROSS-REFERENCE TO RELATED APPLICATIONS

This is a national stage application under 35 U.S.C. §371 of PCT/SE2013/050722, filed Jun. 18, 2013 which claims priority of SE 1250659-8 filed Jun. 19, 2012, the entire contents of each document being incorporated by reference in their entirety.

FIELD OF THE INVENTION

The present invention relates to a method for measuring breath alcohol concentration of a user. The method comprises receiving a flow of an expired breath sample from a user and measuring the pressure of the flow of the expired breath sample. At the same time, the breath sample is led into a fuel cell sensor. The output signal of the fuel cell sensor is used to determine the volume of alcohol present in the breath sample, and thus the breath alcohol concentration.

In a second aspect, the invention also relates to an apparatus for measuring breath alcohol concentration of a user. The apparatus comprises sampling means for receiving an expired breath sample of a user, means for measuring the pressure of the flow of the expired breath sample, a fuel cell sensor and a microcontroller. The microcontroller is adapted to calculate the volume of alcohol present in the breath sample, and thus the breath alcohol concentration, based on an output signal of the fuel cell sensor. In a third aspect, the invention also relates to a breath alcohol interlock device comprising an apparatus for measuring breath alcohol concentration of a user. In a fourth aspect, the invention relates to a vehicle comprising a breath alcohol interlock device.

BACKGROUND OF THE INVENTION

Generally, there are two techniques employed for measuring the breath alcohol concentration and thereby determine a person's blood alcohol concentration. In a first method, infrared spectroscopy is used, whereby a breath sample from a person is subjected to infrared radiation. The molecules in the breath sample absorb specific frequencies, called resonant frequencies, which are characteristic to the molecules. For example the absorption by ethanol molecules gives rise to a specific infrared spectrum which may be used to determine the amount of ethanol present in the breath sample, and thus the breath alcohol concentration. Although this method gives high measuring accuracy, sensors incorporating infrared spectroscopy are expensive, which limits application in mass-produced devices.

A second commonly used technology is based on a fuel cell sensor which converts fuel in the shape of alcohol (ethanol) to electric current in an electrochemical reaction. Fuel cell sensors have a somewhat lower accuracy than infrared spectroscopy sensors, but are much cheaper. However, fuel cell sensors require that the breath sample is of a determinable volume in order to correctly determine the breath alcohol concentration.

Traditional fuel cell based analyser systems operate by means of a mechanical sampling system which draws a pre-specified volume of breath into the fuel cell for analysis. The mechanical means may comprise motors, solenoid valves, piston-cylinder devices, diaphragm mechanisms or push buttons connected to a pump or bellows system. In U.S. Pat. No. 6,167,746 there is disclosed an apparatus comprising an electronically controlled valve to ascertain that a requisite volume of breath is passed through a fuel cell. US 2005/0241871 discloses a sobriety interlock device comprising a pressure transducer and a solenoid valve operating independently of each other providing a variable flow of breath to a fuel cell. A microprocessor instructs the solenoid valve to remain open for a finite period of time to give a predetermined breath sample volume, and calculates an algorithmic correction factor based on pressure readings to provide a pressure compensated alcohol result.

The methods described in the prior art involve advanced control circuitry and complex or bulky mechanical components which introduce extra cost to the system and limit the ability to reduce the size of the system without compromising accuracy.

International application PCT/SE2010/051421, belonging to the applicant, discloses a method and apparatus for measuring breath alcohol concentration overcoming many of the problems associated with the prior art. However, the design of the mouthpiece of the apparatus has shown that there is a non-linear relationship between the flow rate and the final reading. In other words, varying flow rate gives different measurements of breath alcohol concentration, even for similar or identical alcohol concentrations.

Hence, there is a need for improved methods for measuring breath alcohol concentration with high accuracy, which allow for compact devices that may be produced at low cost.

SUMMARY OF THE INVENTION

It is an object of the present invention to provide an improved method for measuring breath alcohol concentration with high accuracy, which allows for compact measuring devices that may be produced at low cost.

According to the present invention, there is provided a method for determining breath alcohol concentration. The method includes the following specific measures. From the measured pressure, the volume of the breath sample is calculated by integrating the pressure over the time of expiration of the breath sample. Throughout the expiration of the breath sample, the breath sample volume and the volume of alcohol present in the breath sample are continually updated by integrating the measured instantaneous pressure and the fuel cell output signal over time. When the user stops blowing, volume compensation is performed wherein the fuel cell output signal is compensated using a stored calibration volume to obtain a volume compensated fuel cell output signal.

By volume compensating the fuel cell output signal, the measuring accuracy of the method and apparatus is ensured, irrespective of the volume of the breath sample. Since the method does not require a predetermined breath sample volume, the mechanical sampling systems as used in the prior art become unnecessary, and the measuring apparatus may be made more compact with fewer or no moving parts. Thereby the size and cost of apparatus may be greatly reduced.

In a further embodiment, the method according to the present invention, comprises calculating the flow rate of the breath sample based on the breath sample volume and the recorded expiration time and compensating the volume compensated fuel cell output signal to obtain a flow rate compensated fuel cell output signal using a stored flow rate adjustment factor corresponding to the calculated flow rate. This allows for the measurements to be adjusted in order to account for variations in flow rate affecting the fuel cell output signal and thereby maintain accurate measurements of breath alcohol concentration.

In an advantageous embodiment, the method according to the present invention comprises measuring the temperature and compensating the compensated fuel cell output signal using a stored temperature adjustment factor corresponding to the measured temperature. This allows for the measurements to be adjusted in order to account for variations in temperature affecting the fuel cell output signal and thereby maintain accurate measurements of breath alcohol concentration.

In a preferred embodiment, the method according to the present invention comprises, if no measurements have been made for a predetermined period of time, performing a calibration by making a measurement of a sample of predetermined volume and concentration, repeating the calibration step at least once and storing the average value of the fuel cell output signal as the calibration volume. This allows for the measurements to be adjusted in order to account for false first high readings of the fuel cell and thereby maintain accurate measurements of breath alcohol concentration.

In preferred embodiments, the method according to the present invention further comprises determining the blood alcohol concentration based on the breath alcohol concentration, and displaying the resulting blood alcohol concentration.

In a preferred embodiment, the method according to the present invention comprises performing the compensation using the formula:

$$FC_{comp} = FC_{out} \cdot \frac{V_{cal}}{V_b}$$

In a further preferred embodiment, the method according to the present invention comprises preventing start-up of a vehicle if the calculated breath alcohol concentration exceeds a predetermined threshold value.

In a further preferred embodiment, the method according to the present invention comprises, measuring the pressure by means of a pressure-based pressure sensor, preferably a Venturi meter or orifice plate in combination with a pressure sensor. The pressure-based pressure sensor has the advantage of providing a compact component with few or no moving parts, ensuring efficient use of space in a device carrying out the method of the invention.

According to one aspect of the present invention, as defined by independent claim 10, there is also provided an apparatus for determining breath alcohol concentration. The apparatus includes the following specific features. Based on the pressure measurements, the microcontroller is adapted to calculate the volume of the breath sample by integrating the pressure over the time of expiration of the breath sample. The microcontroller is further adapted to continually update the breath sample volume and the breath alcohol concentration by integrating the measured instantaneous pressure and the fuel cell output signal over time. The microcontroller is configured to perform volume compensation on the fuel cell output signal to obtain a volume compensated fuel cell output signal, when the user stops blowing.

Preferred embodiments of the apparatus according to the present invention comprise features corresponding to the method described above.

In a preferred embodiment, a breath alcohol interlock device comprising an apparatus for determining breath alcohol concentration according to the present invention and a vehicle comprising such an interlock device are provided.

DETAILED DESCRIPTION OF THE INVENTION

The invention will be further explained below through the detailed description of examples thereof and with reference to the accompanying drawings. It is to be understood that the invention should not be limited to the embodiments shown in the figures and described below, but may be varied to encompass any combination of equivalent features within the scope defined by the attached claims.

Figure 1:
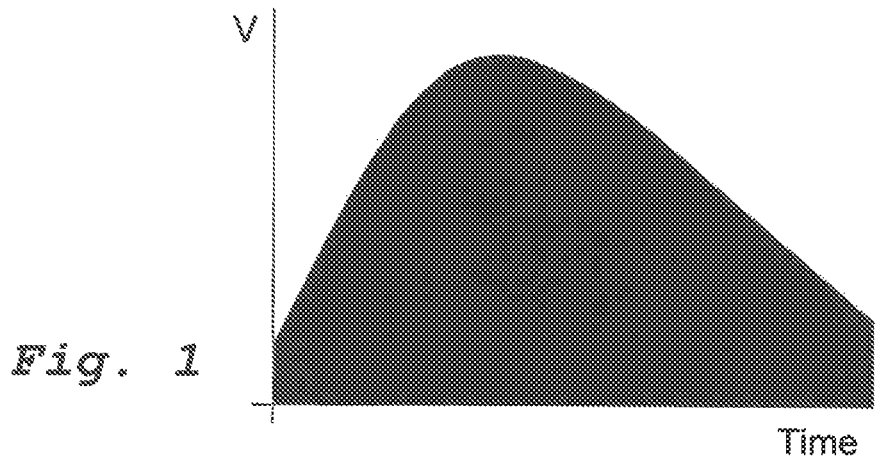
FIG. 1 is a graphical representation of a fuel cell output signal over time.

When an expired breath sample is passed through the fuel cell of a breath alcohol measuring device, also known under the name Breathalyser® (trade mark owned by Dräger), any alcohol (ethanol) present in the breath sample is oxidised in an electrochemical reaction, which generates a measurable electrical current. FIG. 1 shows a typical output response from a fuel cell in a graph of the output voltage versus time. The area under the curve is calculated by integrating the voltage over time, which gives a value FC that is directly proportional to the alcohol concentration in the breath.

In order to give an accurate measurement of the breath alcohol concentration (BrAC), the breathalyser must be calibrated using a sample of predetermined alcohol concentration and volume. When subsequently performing an alcohol breath test on a test person, the breathalyser requires a predetermined sample volume, corresponding to the one used for calibration. When the required volume is supplied, the breathalyser will compare the area under the curve of the fuel cell output signal (voltage) of the test sample with the value stored from the calibration routine and give a reading for the tested breath alcohol concentration.

The requirement of a specific sample volume represents a major inconvenience in breathalysers known in the art. Firstly, if for example the test person has reduced lung capacity, or for some other reason is not able to provide the predetermined volume of breath sample, a valid breath test may not be performed. Secondly, the sampling mechanism needed in a breathalyser to measure and obtain a certain chosen sample volume and to furnish it to the fuel cell (e.g. pressure sensors, valves, pumps, etc.) can be rather expensive and/or bulky, which puts a constraint on the possibilities to minimise the size of the apparatus and to reduce production costs.

In a similar method as when measuring the fuel cell output signal area, the volume of the breath sample can be determined by calculating the area under a curve of the volumetric flow rate of the breath sample, which is directly proportional to the pressure of the flow of the breath sample, versus time. Hence, the same result is achieved by calculating the area under the curve of the pressure, which may be measured in a more straightforward manner. The pressure is readily measured using a suitable pressure sensor, e.g. mechanical, pressure-based, optical, thermal or electromagnetic. In a preferred embodiment of the present invention, a pressure-based pressure sensor is used such as a Venturi meter, orifice plate or equivalent in combination with a pressure sensor. Of course, it is also within the scope of the present invention to measure the flow rate directly.

Laboratory test have proven that the variation of breath volume Vb correlates linearly with the fuel cell output signal FCout for any specified alcohol concentration:

$$FC_{out} = k \cdot V_b$$

By using a measured and stored calibration volume $V_{cal}$, that is the resulting fuel cell output signal when the apparatus is calibrated with a sample of predetermined volume and alcohol concentration, to perform a volume compensation of the fuel cell output signal $FC_{out}$, and substituting the expression for the constant $k = FC_{out}/V_b$ into the corresponding equation, a compensated value for the fuel cell output signal $FC_{comp}$ is obtained:

$$FC_{comp} = FC_{out} \cdot \frac{V_{cal}}{V_b}$$

Hence, a new and inventive method of accurately measuring the breath alcohol concentration of a test person is achieved, capable of handling varied expired volumes of breath, which obviates the need for a sampling mechanism. In other words, the method and apparatus of the present invention is not dependent on the volume of the expired breath sample in that there is no requirement that a threshold for the volume or flow rate is exceeded in order to make a measurement of the breath alcohol concentration.

Another problem encountered when making measurements of breath alcohol concentration is that the fuel cell output signal varies dependent on the flow rate of the expired breath sample. This is i.e., due to the design of the mouthpiece or inlet tube of the apparatus used to make the measurement, which yields a non-linear relationship between the flow rate and the fuel cell output signal.

The flow rate of the expired breath sample may be calculated by dividing the volume of the expired breath sample with the expiration time for the breath sample, i.e. the total time it takes for the user to provide the whole breath sample. Therefore, in the method according to the present invention, the expiration time is recorded to be used in calculating the flow rate.

By obtaining test data for a wide range of different flow rates, using a sample of predetermined volume and alcohol concentration whilst varying the expiration time, it was discovered that the fuel cell output signal as a function of the flow rate corresponds well to a 2nd order polynomial equation. Hence, it is then possible to deduce a flow rate adjustment factor Qf to be used for flow rate compensating the fuel cell output signal for any given flow rate Q. As a result, accurate measurements of breath alcohol concentration may be maintained, even for varying flow rates affecting the fuel cell output signal.

Therefore, in a first step the flow rate of the expired breath sample is calculated as outlined above. Subsequently, flow rate compensation is performed on the fuel cell output signal by multiplying the fuel cell output signal with the flow rate adjustment factor which corresponds to the calculated flow rate, and dividing by the calculated flow rate Q to obtain a flow rate compensated fuel cell output signal.

$$FC_{comp} = FC_{out} \cdot \frac{Q_f}{Q}$$

A further problem which affects the accuracy of the measurement of breath alcohol concentration is the fact that when the apparatus has been left for a period of time, i.e. when no measurements have been made, it will give a false first high measurement even if recalibrated. In order to prevent such first high measurements, it is proposed in to perform the calibration at least twice. After making measurements of at least two samples of predetermined volume and alcohol concentration, the average value of the fuel cell output signal is stored as the calibration volume to be used for future volume compensation. Subsequent measurements of breath alcohol concentration will then maintain the desired accuracy.

It is known that the output signal of the fuel cell varies with the temperature. At decreasing temperatures, the fuel cell output signal also decreases. This may be counteracted by applying temperature compensation to the fuel cell output signal.

By obtaining test data for a wide range of different temperatures, using a sample of predetermined volume and alcohol concentration, it was discovered that the fuel cell output signal as a function of the temperature corresponds well to a 2nd order polynomial equation. Hence, it is then possible to deduce a temperature adjustment factor Tf to be used for temperature compensating the fuel cell output signal for any given temperature. As a result, accurate measurements of breath alcohol concentration may be maintained, even for varying temperatures affecting the fuel cell output signal. Preferably, the range of tested temperatures is between −10 to +50° C.

Therefore, in a first step the temperature of the fuel cell and/or the ambient temperature are measured. Subsequently, temperature compensation is performed on the fuel cell output signal by multiplying the fuel cell output signal with the temperature adjustment factor Tf which corresponds to the measured temperature T, and dividing by the measured temperature T to obtain a temperature compensated fuel cell output signal.

$$FC_{comp} = FC_{out} \cdot \frac{T_f}{T}$$

Still another factor affecting the accuracy of breath alcohol concentration measurements is the known fact that the fuel cell output signal is slowly depleted or saturated with increasing alcohol concentrations. In other words, the fuel cell gives a false lower output signal than what would be expected for the given alcohol concentration.

By obtaining test data for a wide range of different alcohol concentrations, using samples of a predetermined volume and varying alcohol concentrations, it was discovered that the fuel cell output signal as a function of the alcohol concentration is non-linear for alcohol concentrations above about 0.5 mg/l. Hence, it is then possible to deduce a linearity adjustment factor to be used for linearity compensating the fuel cell output signal for any given alcohol concentration. As a result, accurate measurements of breath alcohol concentration may be maintained, even for varying alcohol concentrations affecting the fuel cell output signal. Preferably, only alcohol concentrations above about 0.5 mg/l give rise to linearity compensation.

Figure 2:
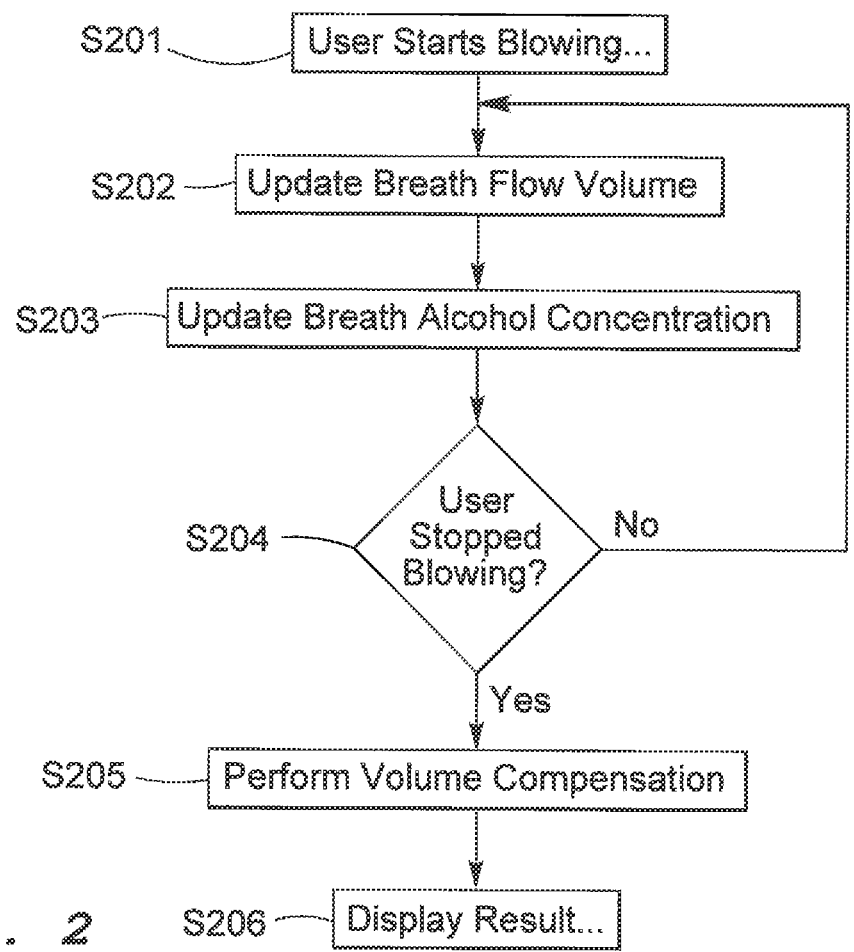
FIG. 2 is a flowchart illustrating the method according to the present invention.

FIG. 2 shows a flowchart illustrating the method according to the present invention. In a first step S201, the user starts blowing into a measuring apparatus, typically by means of a sampling tube or pipe made of plastic or other suitable material which is cheap to produce and replaceable, to ensure hygienic conditions to the users.

As the user continues to blow into the apparatus, the pressure exerted by the flow of the expired breath sample is measured and used to calculate the volume Vb of the breath sample by integrating the measured instantaneous pressure over time. In step S202 the calculated breath volume Vb is continually updated throughout the measuring procedure by integrating the pressure over time.

At the same time, the breath alcohol concentration BrAC is calculated from the fuel cell output signal FCout and is also continually updated in step S202 by integrating the fuel cell output signal FCout over time.

In step S204, it is checked whether the user has stopped blowing. If that is the case, volume compensation is performed in step S205 as explained above, whereby a volume compensated value for the fuel cell output signal FCcomp is obtained and used to calculate a compensated breath alcohol concentration BrACcomp. This value may then be displayed to the user in step S206 and/or used to determine the blood alcohol concentration of the user.

Figure 3:
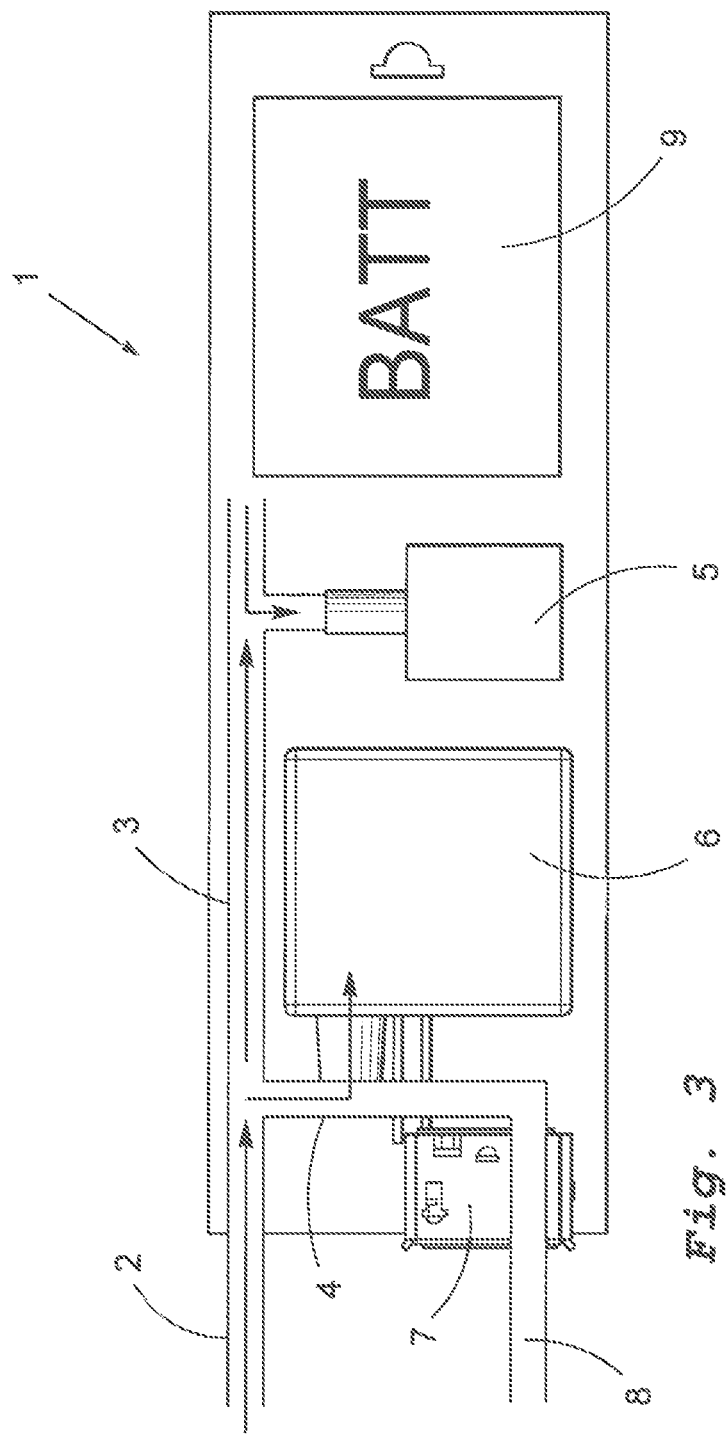
FIG. 3 is a schematic diagram of an apparatus according to the present invention.

FIG. 3 schematically shows an apparatus for measuring breath alcohol concentration BrAC, according to the present invention. The measuring apparatus is contained within a housing 1 and comprises a replaceable breath sample inlet tube 2 for receiving an expired breath sample from a user or test person. Arrows indicate the direction of breath flow through the measuring apparatus. The breath flow is led through a first channel 3 which is closed at a distal end. A pressure sensor 5 is located near the distal end of the first channel 3 and measures the instantaneous pressure of the breath sample through the measuring apparatus 1.

In a preferred embodiment, pressure sensor 5 comprises a pressure-based pressure sensor such as a Venturi meter, an orifice plate or equivalent in combination with a pressure sensor. However the pressure may be measured using any suitable pressure sensor, e.g. mechanical, pressure-based, optical, thermal or electromagnetic.

Part of the breath flow is led through a sampling channel 4 and enters a fuel cell sensor 6 near a proximal end of the first channel 3. Any alcohol (ethanol) present in the breath sample fuels an electrochemical reaction in the fuel cell 6 which gives rise to an electric current. This current then is a measure of the amount of alcohol in the breath sample and represented by a fuel cell output signal FCout, normally the voltage measured across the fuel cell 6.

The pressure sensor 5 and the fuel cell 6 are connected with a microcontroller 7 which comprises means for processing the measurements of the pressure and the fuel cell voltage. In this context, processing incorporates finding the area under the curves of the pressure and the fuel cell output signal FCout versus time. The area corresponds to the volume Vb of the breath sample and the breath alcohol concentration BrAC, respectively. This may also be achieved by integrating the pressure, and the fuel cell output signal FCout, respectively, with respect to time. The microcontroller 7 is adapted to continually update the breath sample volume Vb and the fuel cell output signal FCout throughout the duration of the breath test.

As mentioned above, the flow rate Q is calculated by dividing the volume Vb of the breath sample with the recorded expiration time of the breath sample. For this purpose, the microcontroller 7 comprises clock or timer means. The expiration time may be recorded under the condition that the pressure measured by the pressure sensor 5 is above a predetermined threshold, indicating that a breath sample is being provided.

For measuring the temperature, the measuring apparatus 1 comprises a temperature sensor (not shown). The temperature sensor measures the temperature of the fuel cell and/or the ambient temperature. The microcontroller 7 uses the measured temperature to perform temperature compensation based on a stored temperature adjustment factor corresponding with the measured temperature. Adjustment factors for temperatures in the range −10° C. to +50° C. may be stored in the microcontroller 7.

When the breath sample has passed the fuel cell 6, it exits the housing 1 of the measuring apparatus through an exhaust tube 8.

Also comprised in the measuring apparatus is a battery 9 or other suitable source of energy to power the pressure sensor 5, the fuel cell 6 and/or the microcontroller 7.

In a preferred embodiment of the present invention, the measuring apparatus may further comprise display means to display the measured breath alcohol concentration BrAC and/or the blood alcohol concentration BAC. The blood alcohol concentration BAC may be determined from the blood-to-air partition ratio, i.e. the relation between the amount of alcohol in a given volume of breath and blood. Most breathalysers use an international standard partition ratio of 2100:1, that is, for every part alcohol in the breath there are 2100 parts alcohol in the blood.

The alcohol measuring apparatus according to the present invention may be made very compact and included in a sobriety interlock device. Such interlock devices are known in the art and will not be described in detail here. The interlock device may comprise means for measuring the temperature, humidity and/or alcohol concentration of the breath of a user, and based on these measurements falling within permitted ranges (corresponding to the user being non-intoxicated by alcohol), the interlock device allows starting up of a vehicle or other machinery connected to the interlock device. Further, the interlock device may be equipped with a microprocessor for analysing the results of the alcohol measuring apparatus and a relay electrically connected to the starter of the vehicle or machine.

When provided with an alcohol measuring apparatus according to the present invention, a compact and low-cost sobriety interlock device may be achieved and used to control start-up of any vehicle or machine.

The invention claimed is:

1. A method for measuring breath alcohol concentration (BrAC) of a user, comprising the steps of:
   receiving a flow of an expired breath sample from the user;
   measuring the instantaneous pressure of the flow of the expired breath sample;
   recording the expiration time of the breath sample;
   leading the breath sample into a fuel cell sensor; and
   calculating the breath alcohol concentration (BrAC) based on an output signal ($FC_{out}$) of the fuel cell sensor;
   calculating the volume ($V_b$) of the breath sample based on the measured pressure;
   updating continually the breath sample volume ($V_b$) and the breath alcohol concentration (BrAC) by integrating the measured instantaneous pressure and the fuel cell output signal ($FC_{out}$) over time, irrespective of the breath sample volume ($V_b$);
   calculating the flow rate (Q) of the breath sample based on the breath sample volume ($V_b$) and the recorded expiration time; and
   when the user stops blowing, performing the following steps before calculating the final breath alcohol concentration (BrAC):
   compensating the fuel cell output signal ($FC_{out}$) using a stored calibration volume ($V_{cal}$) to obtain a volume compensated fuel cell output signal ($FC_{Vcomp}$), compensating the volume compensated fuel cell output signal ($FC_{Vcomp}$) to obtain a flow rate compensated fuel cell output signal ($FC_{Qcomp}$) using a stored flow rate adjustment factor ($Q_f$) corresponding to the calculated flow rate (Q)

measuring a temperature (T); and compensating the compensated fuel cell output signal using a stored temperature adjustment factor ($T_f$) corresponding to the measured temperature.

2. The method according to claim 1, further comprising the steps of, if no measurements have been made for a predetermined period of time:

performing a calibration by making a measurement of a sample of predetermined volume and concentration;

repeating the calibration step at least once; and storing the average value of the fuel cell output signal ($FC_{out}$) as the calibration volume ($V_{cal}$).

3. The method according to claim 1, further comprising the step of:

determining the blood alcohol concentration (BAC) based on the breath alcohol concentration (BrAC).

4. The method according to claim 3, further comprising the step of:

displaying the resulting blood alcohol concentration (BAC).

5. The method according to claim 1, wherein said volume compensating is performed using the formula:

$$FC_{comp} = FC_{out} \cdot \frac{V_{cal}}{V_b}.$$

6. The method according to claim 1, further comprising the step of:

preventing start-up of a vehicle if the calculated breath alcohol concentration (BrAC) exceeds a predetermined threshold value.

7. The method according to claim 1, wherein the pressure is measured by means of a pressure-based pressure sensor.

8. Apparatus for measuring breath alcohol concentration (BrAC), comprising:

means for receiving an expired breath sample of a user;

means for measuring the instantaneous pressure of the flow of the expired breath sample;

means for recording the expiration time of the breath sample;

a fuel cell sensor; and a microcontroller adapted to:

calculate the breath alcohol concentration (BrAC) based on an output signal ($FC_{out}$) of the fuel cell sensor;

calculate the volume ($V_b$) of the breath sample based on the measured pressure; wherein the microcontroller is further adapted to:

continually update the breath sample volume ($V_b$) and the breath alcohol concentration (BrAC) by integrating the measured instantaneous pressure and the fuel cell output signal ($FC_{out}$) over time, irrespective of the breath sample volume ($V_b$); and calculate the flow rate (Q) of the breath sample based on the breath sample volume ($V_b$) and the recorded expiration time;

perform a volume compensation on the fuel cell output signal ($FC_{out}$) to obtain a volume compensated fuel cell output signal ($FC_{Vcomp}$) using a stored calibration volume ($V_{cal}$), perform a flow rate compensation on the volume compensated fuel cell output signal ($FC_{Vcomp}$) to obtain a flow rate compensated fuel cell output signal ($FC_{Qcomp}$) using a stored flow rate adjustment factor ($Q_f$) corresponding to the calculated flow rate (Q), and means for measuring the temperature (T), and wherein the microcontroller is further adapted to:

compensate the compensated fuel cell output signal using a stored temperature adjustment factor ($T_f$) corresponding to the measured temperature (T).

9. The apparatus according to claim 8, adapted to be calibrated by making a measurement of a sample of predetermined volume and concentration at least two times if no measurements have been made for a predetermined period of time, and wherein the microcontroller is further adapted to:

store the average value of the fuel cell output signal ($FC_{out}$) as the calibration volume ($V_{cal}$).

10. The apparatus according to claim 8, wherein the microcontroller is further adapted to determine the blood alcohol concentration (BAC) based on the breath alcohol concentration (BrAC).

11. The apparatus according to claim 8, wherein the apparatus further comprises display means to display the resulting blood alcohol concentration (BAC).

12. The apparatus according to claim 8, wherein said volume compensation is performed using the formula:

$$FC_{comp} = FC_{out} \cdot \frac{V_{cal}}{V_b}.$$

13. The apparatus according to claim 8, wherein the means for measuring the pressure comprises a pressure-based pressure sensor.

14. A breath alcohol interlock device comprising an apparatus according to claim 8.

15. A vehicle comprising a breath alcohol interlock device according to claim 14.

16. The method according to claim 7, wherein the pressure is measured by one of a Venturi meter or orifice plate in combination with a pressure sensor.

17. The apparatus according to claim 13, wherein the pressure based pressure sensor comprises one of a Venturi or orifice plate in conjunction with a pressure sensor.

* * * * *